(12) United States Patent
Kärcher et al.

(10) Patent No.: US 10,842,584 B2
(45) Date of Patent: Nov. 24, 2020

(54) COMPONENT FOR A MEDICAL INSTRUMENT AND MEDICAL INSTRUMENT

(71) Applicant: Karl Storz GmbH & Co. KG, Tuttlingen (DE)

(72) Inventors: Daniel Kärcher, Tuttlingen (DE); Jochen Stefan, Tuttlingen (DE)

(73) Assignee: Karl Storz GmbH & Co. KG, Tuttlingen (DE)

(*) Notice: Subject to any disclaimer, the term of this patent is extended or adjusted under 35 U.S.C. 154(b) by 436 days.

(21) Appl. No.: 15/717,068

(22) Filed: Sep. 27, 2017

(65) Prior Publication Data

US 2018/0085181 A1   Mar. 29, 2018

(30) Foreign Application Priority Data

Sep. 28, 2016   (DE) .................. 10 2016 118 304

(51) Int. Cl.
*A61B 90/00* (2016.01)
*A61B 17/29* (2006.01)
*A61B 17/00* (2006.01)
*A61B 34/00* (2016.01)

(52) U.S. Cl.
CPC .............. *A61B 90/03* (2016.02); *A61B 17/29* (2013.01); *A61B 34/70* (2016.02); *A61B 2017/0034* (2013.01); *A61B 2017/0046* (2013.01); *A61B 2017/00526* (2013.01); *A61B 2017/2902* (2013.01); *A61B 2017/2905* (2013.01); *A61B 2090/034* (2016.02); *A61B 2217/007* (2013.01)

(58) Field of Classification Search
CPC .... A61B 2017/0046; A61B 2017/0034; A61B 90/03
See application file for complete search history.

(56) References Cited

U.S. PATENT DOCUMENTS 4,569,131 A * 2/1986 Falk ................. A61B 17/29
                                                  30/251
5,849,022 A * 12/1998 Sakashita ............ A61B 17/29
                                                  606/174

(Continued)

FOREIGN PATENT DOCUMENTS

DE       83 16 034 U1    9/1983
DE      197 31 453 A1    2/1999

(Continued)

*Primary Examiner* — Gary Jackson
*Assistant Examiner* — Zahed Kabir
(74) *Attorney, Agent, or Firm* — McGlew and Tuttle, P.C.

(57) ABSTRACT

A component (14) for a medical instrument includes a shaft (15), a transmission device (16), which is movable in the shaft (15), for transmitting a force from a manipulation device (18) coupled to the proximal end of the component (14) to a tool (13) at the distal end of the component (14), an abutment surface (86) on the shaft (15), and an abutment surface (36) on the transmission device (16). The abutment surface (86) of the shaft (15) and the abutment surface (36) of the transmission device (16) are arranged such that a mechanical contact between the abutment surface (36) of the transmission device (16) and the abutment surface (86) of the shaft (15) limits a movement of the transmission device (16) relative to the shaft (15) in the proximal direction.

19 Claims, 5 Drawing Sheets (56) References Cited

U.S. PATENT DOCUMENTS

| | | | | |
|---|---|---|---|---|
| 2006/0259043 A1* | 11/2006 | Miyamoto | ......... | A61B 17/0469 606/139 |
| 2009/0292262 A1* | 11/2009 | Adams | ................. | A61F 2/2436 604/264 |
| 2013/0053835 A1* | 2/2013 | Bacher | ................... | A61B 17/29 606/1 |
| 2013/0123800 A1* | 5/2013 | Leroy | .............. | A61B 17/00234 606/130 |
| 2016/0151071 A1* | 6/2016 | Tokarz | ............... | A61B 17/1285 606/143 |

FOREIGN PATENT DOCUMENTS

| | | |
|---|---|---|
| DE | 10 2006 034 590 A1 | 2/2007 |
| DE | 10 2009 031 262 A1 | 1/2011 |
| DE | 10 2011 007 119 A1 | 10/2012 |
| DE | 10 2011 007 121 A1 | 10/2012 |
| DE | 10 2012 002 770 A1 | 8/2013 |
| EP | 0 925 037 B1 | 12/2003 |
| EP | 2 269 522 A1 | 1/2011 |
| EP | 2 510 888 A1 | 10/2012 |
| EP | 2 510 889 A1 | 10/2012 |
| EP | 2 561 816 A1 | 2/2013 |
| EP | 2 626 018 A2 | 8/2013 |
| WO | 99/04703 A1 | 2/1999 |

\* cited by examiner

Fig. 16

COMPONENT FOR A MEDICAL INSTRUMENT AND MEDICAL INSTRUMENT

CROSS REFERENCE TO RELATED APPLICATIONS

This application claims the benefit of priority under 35 U.S.C. § 119 of German Application 10 2016 118 304.0, filed Sep. 28, 2016.

FIELD OF THE INVENTION

The present invention relates to a component for a medical instrument and to a medical instrument. The present invention relates in particular to measures which, under certain circumstances, are able to prevent destruction of a medical instrument through improper use or handling.

BACKGROUND OF THE INVENTION

DE 197 31 453 A1 (similar or identical: WO 99/04703 A1 and EP 0 925 037 B1) describes a surgical instrument 10 with a device 30 for limiting the transmission of force (column 7, lines 39 to 41). This device 30 connects a first portion 32 and a second portion 54 of an otherwise rod-shaped actuation element 26 (FIGS. 1 and 2). The device 30 comprises an approximately hollow cylindrical housing 38 which is rigidly connected to the first portion 32 of the rod-shaped actuation element 26 and which has axially extending grooves (column 7, lines 45 to 55) and an inner cone (column 8, lines 14 to 16; FIG. 4). The device 30 moreover comprises a cone 56 which is connected to the second portion 54 of the rod-shaped actuation element 26, has a conical wedge surface 57 and is arranged in the hollow cylindrical housing 38 such that the cone 56 bears on the inner cone 64 (column 8, lines 7 to 23). When a predetermined force is exceeded, the hollow cylindrical housing 38 is deformed and the cone 56 is pulled partially out of the latter (column 8, lines 33 to 53).

DE 10 2009 031 262 A1 and EP 2 269 522 A1 describe a medical instrument 1 in which a force-limiting device 8 is provided in the handle 3, and, when a threshold load is exceeded, the components coupled to each other are separated reversibly by the force-limiting device 8 (paragraph [0024] of EP 2 269 522 A1).

DE 10 2011 007 121 A1, EP 2 510 888 A1, DE 10 2011 007 119 A1 and EP 2 510 889 A1 describe a manipulation device for an instrument used in microinvasive surgery. A pretensioned compression spring 564 in a cup-shaped structural part 562 limits a tensile force that is to be transmitted from a rod 561 to a transmission bar 40 (paragraph [0083] of EP 2 510 888 A1; FIG. 3).

DE 10 2012 002 770 A1 and EP 2 626 018 A2 describe a medical instrument in which a force-limiting device 8 is provided in the handle 3 and reversibly limits the transmitted force when a threshold load is exceeded (paragraph [0026] of EP 2 626 018 A2).

SUMMARY OF THE INVENTION

It is an object of the present invention to make available an improved component for a medical instrument, an improved medical instrument, and an improved method for producing a component for a medical instrument.

According to the invention, a component for a medical instrument comprises a shaft, a transmission device, which is movable in the shaft, for transmitting a force from a manipulation device coupled to the proximal end of the component to a tool at the distal end of the component, an abutment surface on the shaft, and an abutment surface on the transmission device. The abutment surface of the shaft and the abutment surface of the transmission device are arranged such that a mechanical contact between the abutment surface of the transmission device and the abutment surface of the shaft limits a movement of the transmission device relative to the shaft in the proximal direction.

The component is provided and designed to be mechanically connected and/or coupled to one or more further components such that a medical instrument is formed. The component is in particular a component for a microinvasive medical instrument, wherein the shaft has a diameter of a few millimeters or less and a length of a few centimeters or less or a few decimeters. For example, the shaft can be provided and designed to be inserted into a working channel of an endoscope.

The proximal end of the shaft is provided and designed in particular to be mechanically connected to a manipulation device in such a way as to be releasable without destruction, or connected thereto permanently, i.e. such that it is not releasable without destruction. The proximal end of the transmission device is provided and designed in particular to be mechanically coupled to a manually movable part of a manipulation device in such a way as to be releasable without destruction, or connected thereto permanently, i.e. such that it is not releasable without destruction.

At its distal end, the component can have a tool which is in particular rigidly connected to the distal end of the shaft and which has a movable part (for example a pivotable branch or a pivotable jaw part). The movable part of the tool is mechanically coupled directly or indirectly to the distal end of the transmission device in such a way that a movement of the transmission device relative to the shaft brings about a movement of the movable part of the tool relative to another part of the tool. The tool can be mechanically connected and coupled to the distal end of the shaft and to the distal end of the transmission device in such a way as to be releasable without destruction, or connected thereto permanently, i.e. such that it is not releasable without destruction.

Alternatively, the component may have no tool and may instead be provided and designed for mechanically connecting and coupling a tool to the distal end of the shaft, and to the distal end of the transmission device, in such a way as to be releasable without destruction, or for connecting it permanently, i.e. such that it is not releasable without destruction.

The transmission device is movable relative to the shaft particularly in a direction parallel to the longitudinal axis of the shaft. The transmission device is in particular provided and designed to transmit a tensile force from a movable part of a manipulation device coupled to the proximal end of the transmission device to a movable part of a tool coupled to the distal end of the transmission device. Alternatively or in addition, the transmission device can be provided and designed to transmit a shearing force from a movable part of a manipulation device coupled to the proximal end of the transmission device to a movable part of a tool coupled to the distal end of the transmission device.

The distal end of the transmission device is in particular couplable or coupled to a movable part of a tool in such a way that a movement of the transmission device in the proximal direction brings about the intended working movement of the movable part of the tool. In this case, the force needed for the working movement of the movable part of the tool is transmitted by a tensile force or tensile stress in the transmission device. The working movement of the movable part of a tool is the movement in which the tool performs the intended work. In the case of forceps or another tool for gripping, holding, squeezing, punching or cutting, this is generally the closing movement in which two (in some cases more) jaw parts or branches are moved toward each other. In other cases, the working movement can be a movement in which jaw parts or branches are moved away from each other, for example in a tool for expanding or widening a vessel or another cavity.

As an alternative to an arrangement of the abutment surface of the shaft and the abutment surface of the transmission device in which a mechanical contact between the abutment surface of the transmission device and the abutment surface of the shaft limits a movement of the transmission device relative to the shaft in the proximal direction, it is possible for the abutment surface of the shaft and the abutment surface of the transmission device to be arranged in such a way that a mechanical contact between the abutment surface of the transmission device and the abutment surface of the shaft limits a movement of the transmission device relative to the shaft in the distal direction.

In a component as described here, the abutment surface of the shaft is in particular oriented distally and the abutment surface of the transmission device oriented proximally.

In a component as described here, the movement of the distal end of the transmission device relative to the distal end of the shaft is limited, and the abutment surface of the shaft and the abutment surface of the transmission device arranged, such that a mechanical contact between the abutment surface of the transmission device and the abutment surface of the shaft limits an elastic deformation of the transmission device, caused by a force transmitted by the transmission device, to a predetermined maximum value, wherein the predetermined maximum value of the elastic deformation and elastic properties of the transmission device are chosen such that, at the force present at the predetermined maximum value of the elastic deformation of the transmission device, destruction or damage of the shaft, the transmission device and a tool connected to the distal end of the shaft and coupled to the distal end of the transmission device is excluded.

The movement of the distal end of the transmission device relative to the distal end of the shaft is in particular limited by a tool which is mechanically connected to the distal end of the shaft and mechanically coupled to the distal end of the transmission device. If the component comprises no tool at the distal end, but is instead provided and designed for mechanical connection and coupling to a tool, the movement of the distal end of the transmission device relative to the distal end of the shaft is in particular only then limited in the proximal direction or only then in so far as is necessary for the described limiting of the transmitted force to the predetermined maximum value if the distal end of the shaft is connected to the tool provided for the component, or to one of several tools provided for the component, in the intended manner and if one or more movable parts of the tool are mechanically coupled in the intended manner to the distal end of the transmission device.

In a component as described here, the abutment surface of the shaft and the abutment surface of the transmission device are in particular arranged such that a mechanical contact between the abutment surface of the transmission device and the abutment surface of the shaft in the intended use limits an elastic deformation of the transmission device, by a force transmitted by the transmission device, to a predetermined maximum value, wherein the predetermined maximum value of the elastic deformation and elastic properties of the transmission device are chosen such that, at the force present at the predetermined maximum value of the elastic deformation of the transmission device, destruction or damage of the shaft, the transmission device and a tool connected to the distal end of the shaft and coupled to the distal end of the transmission device is excluded.

A plastic deformation of the transmission device, the shaft or a tool coupled to the distal end of the shaft and to the distal end of the transmission device is also a damage of the transmission device, the shaft or of the tool. Exclusion of destruction or damage of the shaft, the transmission device and a tool coupled to the distal end of the shaft and to the distal end of the transmission device thus also means that the transmission device, the shaft and the tool are each deformed only elastically, not plastically.

In a component as described here, destruction or damage of the shaft, the transmission device and a tool coupled to the distal end of the shaft is in particular also excluded when the tool is blocked in a fully opened or in a fully closed state or in any desired state.

A tool connected to the distal end of the shaft and coupled to the distal end of the transmission device and used for cutting, gripping, holding, squeezing or punching can, for example, be blocked in its fully opened configuration by a hard object or by an object that does not yield at the force that can be generated. If the transmission device is coupled to the movable part of the tool in such a way that, in order to close the tool, a tensile force needs to be transmitted by the transmission device, the transmission device is then maximally deformed, i.e. tensioned, when the tool is blocked in the fully opened state and the abutment surface of the transmission device bears on the abutment surface of the shaft. The abutment surface of the transmission device and the abutment surface of the shaft are positioned, and the elastic properties of the transmission device chosen, such that in this case too the shaft, the transmission device and a tool coupled to the distal end of the shaft are not damaged or destroyed.

In a component as described here, the abutment surface of the shaft is arranged near the proximal end of the shaft, and the abutment surface of the transmission device is arranged near the proximal end of the transmission device.

The distance of the abutment surface of the shaft from the proximal end of the shaft is in particular not more than one fifth or not more than one tenth of the length of the shaft. The distance of the abutment surface of the transmission device from the proximal end of the transmission device is in particular not more than one fifth or not more than one tenth of the length of the transmission device.

In a component as described here, the abutment surface of the shaft and the abutment surface of the transmission device are in particular arranged in a proximal region of the shaft in which the shaft has an increased diameter or an increased cross section.

In a component as described here, the abutment surface of the shaft and the abutment surface of the transmission device are in particular arranged in a region of the shaft that is intended to be received in a manipulation device.

The shaft has in particular a long and thin tubular portion and, compared to the tubular portion, a much thicker proximal portion. The long and thin tubular portion of the shaft generally extends along at least two thirds or at least four fifths or at least nine tenths of the length of the shaft and has a diameter of a few millimeters or less. The diameter and cross section of the proximal portion of the shaft are generally much greater than the diameter and cross section of the long and thin tubular portion. In the proximal portion, more installation space is available for the abutment surface of the shaft and for the abutment surface of the transmission device.

In a component as described here, the transmission device has its minimum cross-sectional surface area in particular in a portion lying distally with respect to the abutment surface of the transmission device, wherein all the cross-sectional surface areas of the transmission device lying proximally with respect to the abutment surface of the transmission device are greater than the minimum cross-sectional surface area of the transmission device.

The cross-sectional surface area of the transmission device is in particular much greater proximally with respect to the abutment surface of the transmission device than it is distally with respect to the abutment surface of the transmission device. For example, the cross-sectional surface area of the transmission device, proximally with respect to the abutment surface of the transmission device, is continuously greater, at least by a factor of 5 or at least by a factor of 10 or at least by a factor of 20, than it is distally with respect to the abutment surface of the transmission device. The transmission device has, in particular distally with respect to the abutment surface of the transmission device, a substantially constant circular cross section with a diameter of less than 1 mm. Proximally with respect to the abutment surface of the transmission device, the transmission device has, in particular continuously, a circular or other cross section with a cross-sectional surface area of several square millimeters.

A configuration of the transmission device in which its cross-sectional surface area proximally with respect to the abutment surface of the transmission device is much greater than distally permits great robustness of the transmission device proximally with respect to the abutment surface of the transmission device and, consequently, a low risk of destruction of damage caused by an excessive force.

In a component as described here, the transmission device has its minimum tensile strength in particular in a portion lying distally with respect to the abutment surface of the transmission device, wherein the tensile strength of the transmission device proximally with respect to the abutment surface of the transmission device is continuously greater than the minimum tensile strength of the transmission device.

The tensile strength of the transmission device proximally with respect to the abutment surface of the transmission device is in particular much greater than the minimum tensile strength of the transmission device. For example, the tensile strength of the transmission device proximally with respect to the abutment surface of the transmission device is greater, at least by a factor of 5 or by a factor of 10 or by a factor of 20 than the minimum tensile strength of the transmission device.

In a component as described here, the transmission device is elastically deformable up to a first maximum force in particular distally with respect to the abutment surface of the transmission device, wherein the transmission device proximally with respect to the abutment surface of the transmission device is elastically deformable up to a second maximum force, and wherein this second maximum force is greater than the first maximum force.

The maximum force up to which the transmission device is elastically deformable at a defined point is the greatest force at which the transmission device is still not plastically deformed at the defined point. The second maximum force is in particular much greater than the first maximum force. The second maximum force is in particular greater than the first maximum force at least by a factor of 2 or at least by a factor of 5 or at least by a factor of 10 or at least by a factor of 20 or at least by a factor of 50.

Through the configuration and arrangement of the abutment surface of the transmission device and of the abutment surface of the shaft and the choice of elastic properties of the transmission device, it is possible to prevent destruction or damage of the transmission device and of the shaft and of a tool at the distal end of the component. If the transmission device has much greater mechanical robustness proximally with respect to the abutment surface of the transmission device, it is also possible to considerably reduce the risk of destruction or damage of the transmission device proximally with respect to the abutment surface of the transmission device.

In a component as described here, the transmission device cannot be removed from the shaft, in particular neither proximally nor distally, without dismantling the shaft.

A component as described here moreover comprises in particular a further abutment surface on the shaft and a further abutment surface on the transmission device, wherein the further abutment surface of the shaft and the further abutment surface of the transmission device are arranged such that a mechanical contact between the further abutment surface of the transmission device and the further abutment surface of the transmission device limits a movement of the transmission device relative to the shaft in the distal direction.

The further abutment surface of the shaft is arranged in particular near the proximal end of the shaft and in particular near the abutment surface of the shaft. The further abutment surface of the transmission device is arranged in particular near the proximal end of the transmission device. In particular, the further abutment surface of the shaft is oriented proximally and the further abutment surface of the transmission device is oriented distally.

The limiting of the movement of the transmission device relative to the shaft in the distal direction can prevent overloading, damage or destruction of the transmission device, the shaft or a tool at the distal end of the component, e.g. caused by an excessive shearing force transmitted by the transmission device. In particular, it is possible to prevent compression of the transmission device distally with respect to the further abutment surface of the transmission device.

In a component as described here, the transmission device has in particular an outwardly protruding collar, wherein the shaft has a groove that widens a channel in which the transmission device is arranged, wherein the collar of the transmission device is arranged in the groove of the shaft, and wherein the abutment surface of the transmission device is part of the surface of the collar.

A proximally oriented surface of the collar can form the abutment surface of the transmission device, while a distally oriented surface of the groove can form the abutment surface of the shaft. A distally oriented surface on the collar can form the further abutment surface of the transmission device, while a proximally oriented surface in the groove can form the further abutment surface of the shaft, in order to limit a movement of the transmission device relative to the shaft in the distal direction.

The collar is in particular ring-shaped or circular ring-shaped. In this case, a ring-shaped or circular ring-shaped region of the surface of the collar in particular forms the abutment surface of the transmission device.

The groove is in particular ring-shaped or circular ring-shaped and provides a ring-shaped widening of the channel in which the transmission device is arranged. In this case, a ring-shaped or circular ring-shaped region of the surface of the groove in particular forms the abutment surface of the shaft.

In a component as described here, the transmission device has in particular a projection, a lug, a web, a peg or another convex region, wherein the shaft has a groove or another niche-shaped recess which issues from a channel in which the transmission device is arranged, wherein the projection or the lug or the web or the peg or the other convex region of the transmission device is arranged in the groove or the other niche-shaped recess of the shaft, wherein the abutment surface of the shaft is part of the inner surface of the groove or of the other niche-shaped recess of the shaft, and wherein the abutment surface of the transmission device is part of the surface of the projection or of the lug or of the web or of the peg or of the other convex region.

Moreover, a further proximally oriented part of the inner surface of the groove or of the other niche-shaped recess of the shaft can form a further abutment surface of the shaft, and a further distally oriented part of the surface of the projection or of the lug or of the web or of the peg or of the other convex region can form a further abutment surface of the transmission device, in order to limit a movement of the transmission device relative to the shaft in the distal direction.

A component as described here moreover comprises in particular a tool at the distal end of the shaft, wherein the tool has a movable part which is coupled to the distal end of the transmission device.

The tool can be connected to the distal end of the shaft so as to be releasable without destruction or can be connected thereto permanently, i.e. so as not to be releasable without destruction. The tool is in particular designed for gripping, holding, squeezing, cutting or punching. The movable structural part is in particular a branch or a jaw part of the tool. The movable structural part is in particular coupled to the transmission device in such a way that a linear translational movement of the transmission device in a direction parallel to its longitudinal axis brings about a pivoting movement of the movable jaw part.

A medical instrument comprises a component, as described here, and a manipulation device which is coupled or couplable to the proximal end of the shaft.

A method for producing a component for a medical instrument comprises a step of guiding a proximal end of a first structural part of a transmission device from the distal direction through a first structural part of a shaft as far as an assembly position which, relative to the first structural part of the shaft, lies proximally with respect to the position provided for the finished component, a step of mechanically connecting the proximal end of the first structural part of the transmission device to a second structural part of the transmission device, and a step of moving the proximal end of the first structural part of the transmission device in the distal direction, relative to the first structural part of the shaft, as far as a position provided for the finished component.

The method is suitable in particular for producing a component as described here or another component with the here described features, properties and functions. The steps of guiding through, connecting and moving are in particular performed in this order. The proximal end of the first structural part of the transmission device is in particular connected to the second structural part of the transmission device permanently, i.e. so as not to be releasable without destruction. The second structural part of the transmission device, with which the proximal end of the first structural part is connected to the transmission device, and the first structural part of the shaft are in particular designed such that a movement of the second structural part of the transmission device relative to the first structural part of the shaft is limited in the distal direction by mechanical contact of corresponding abutment surfaces.

A method as described here moreover comprises in particular a step of inserting a proximal end of a shaft tube into the first structural part of the shaft as far as an assembly position which, relative to the first structural part of the shaft, lies proximally with respect to the position provided for the finished component, before connecting the proximal end of the first structural part of the transmission device to the second structural part of the transmission device, a step of moving the proximal end of the shaft tube relative to the first structural part of the shaft in the distal direction as far as the position of the shaft tube provided for the use of the component, after connecting the proximal end of the first structural part of the transmission device to a second structural part of the transmission device, and a step of mechanically connecting the proximal end of the shaft tube to the first structural part of the shaft at the position provided for the finished component relative to the first structural part of the shaft.

The proximal end of the shaft tube is in particular connected to the first structural part of the shaft permanently, i.e. so as not to be releasable without destruction.

A method as described here comprises in particular a step of coupling a distal end of the transmission device to a movable part of a tool and a step of mechanically connecting the tool to a distal end of the shaft.

In a method as described here, in particular at least either the step of coupling the distal end of the transmission device to a movable part of the tool or the step of mechanically connecting the tool to the distal end of the shaft is carried out at least either before the step of inserting the proximal end of the shaft tube into the first structural part of the shaft or before the step of guiding the proximal end of the first structural part of the transmission device from the distal direction through the first structural part of the shaft.

The present invention is described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
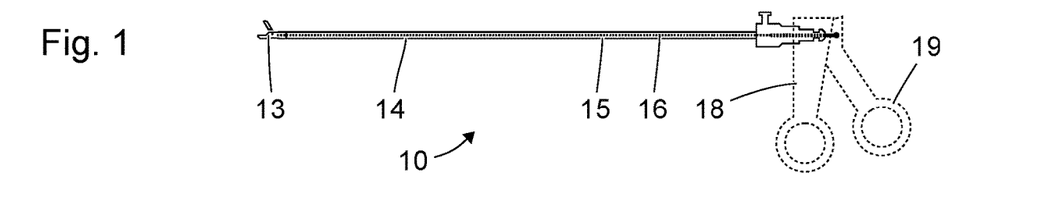
FIG. 1 is a schematic view of a medical instrument.

Referring to the drawings, FIG. 1 shows a schematic view of a medical instrument 10 with a tool 13 at the distal end of a component 14. The tool 13 in FIG. 1 is indicated by way of example as a tool for the gripping, holding, squeezing, cutting or punching of tissue between a stationary branch and a pivotable branch.

The component 14 comprises a shaft 15 which can be straight or curved, rigid or elastic. The shaft 15 is in particular flexible and has a circular cross section with a diameter of 2 mm or less. The component 14 moreover comprises a transmission device 16 for transmitting a force. The transmission device 16 is arranged in the interior of the shaft 15 and is therefore not actually visible, and it is thus indicated in FIG. 1 only by a broken line.

The proximal end of the shaft 15 has a considerably larger cross section and is mechanically connected to a manipulation device 18. The manipulation device 18 has a manually movable part 19. The movable part 19 is coupled to the proximal end of the transmission device 16 in such a way that a pivoting movement of the movable part 19 (in particular about a pivot axis orthogonal to the drawing plane of FIG. 1) relative to the rest of the manipulation device 18 brings about a movement, in particular a translation, of the transmission device 16 relative to the shaft 15. The distal end of the transmission device 16 is coupled to the movable part of the tool 13 in such a way that a movement of the transmission device 16 relative to the shaft 15 brings about a pivoting movement of the movable part of the tool 13 relative to the rest of the tool 13.

The component 14 is separable from the manipulation device 18 without destruction, wherein at the same time the mechanical coupling of the proximal end of the transmission device 16 to the movable part 19 of the manipulation device 18 is ended. The component 14 is thus designed to form the medical instrument 10 in conjunction with the manipulation device 18.

Figure 2:
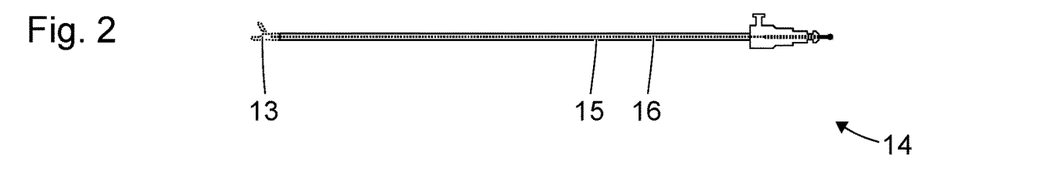
FIG. 2 is a schematic view of a component of a medical instrument.

FIG. 2 shows a schematic view of a further component 14 for a medical instrument. In terms of certain features, properties and functions, the component 14 is similar to the component shown in FIG. 1. In particular, the proximal end of the shaft 15 can be mechanically connected to a manipulation device in such a way as to be releasable without destruction, or it can be connected thereto permanently, i.e. such that it is not releasable without destruction, and the proximal end of the transmission device 16 can be mechanically coupled to a movable part of the manipulation device in such a way as to be releasable without destruction, or it can be connected thereto permanently, i.e. such that it is not releasable without destruction.

The component 14 shown in FIG. 2 differs from the component shown in FIG. 1 in particular in that it has no tool at the distal end and instead can only be connected or coupled to a tool 13. The tool 13 is therefore indicated by broken lines. The distal end of the shaft 15 of the component 14 can be provided and designed to be mechanically connected to a stationary part of the tool 13 in such a way as to be releasable without destruction, or it can be connected thereto permanently, i.e. such that it is not releasable without destruction. The distal end of the transmission device 16 can be provided and designed to be mechanically coupled to a movable part of the tool 13 in such a way as to be releasable without destruction, or it can be connected thereto permanently, i.e. such that it is not releasable without destruction.

Figure 3:
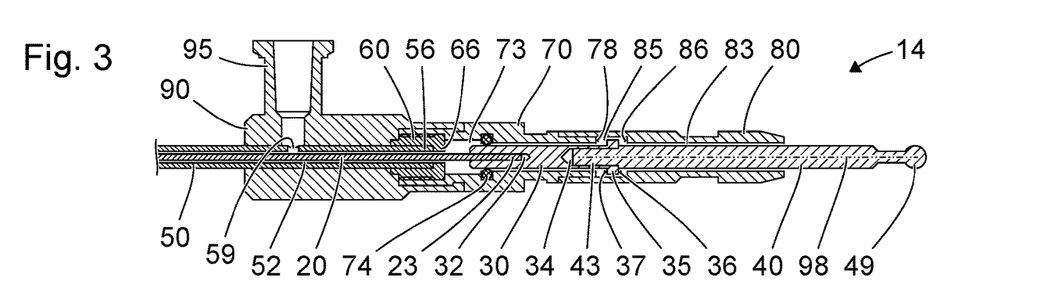
FIG. 3 is a schematic view of a section through the proximal end of a component of a medical instrument.

FIG. 3 shows a schematic view of a section through a proximal end of a component 14 for forming a medical instrument. The component 14 shown in FIG. 3 is similar to the components shown in FIGS. 1 and 2 in terms of certain features, properties and functions, particularly those not shown in FIGS. 3 to 5.

In the component 14 shown in FIG. 3, a transmission device (cf. reference sign 16 from FIGS. 1 and 2) comprises, from the distal end (on the left in FIG. 3) to the proximal end (on the right in FIG. 3), a wire 20 as a log thin portion of the transmission device, a first rod part 30 and a second rod part 40. In the component 14 shown in FIG. 3, the shaft (cf. reference sign 15 from FIGS. 1 and 2) comprises, from the distal end to the proximal end, a long thin shaft tube 50, a first sleeve part 60, a second sleeve part 70 and a third sleeve part 80. The proximal end of the shaft tube 50, the first sleeve part 60 and the distal end of the second sleeve part 70 are moreover surrounded by a connector part 90.

The wire 20 has the shape of a long thin cylinder, in particular a circular cylinder. The wire 20 is provided and designed to transmit a force to a tool at the distal end of the component 14. The wire 20 is formed in particular from surgical steel, spring steel or another metal. Alternatively, the wire can be produced from plastic or can contain a plastic.

The proximal end 23 of the wire 20 is arranged in a first longitudinal bore 32 at the distal end of the first rod part 30 and is mechanically connected rigidly thereto, for example by welding, soldering or adhesive bonding, or in another way involving material bonding or force-fit and/or form-fit engagement. At its proximal end, the first rod part 30 has a second longitudinal bore 34, in which a peg 43 at the distal end of the second rod part is arranged. The peg 43 at the distal end of the second rod part is mechanically connected rigidly to the second longitudinal bore 34 at the proximal end of the first rod part 30, for example by a screw connection between corresponding inner and outer threads and/or in another way. At its proximal end, the second rod part 40 has a coupling ball 49 for releasable mechanical coupling to a movable part 19 of a manipulation device 18 (cf. FIG. 1).

The first rod part 30 moreover has a collar 35. In the example shown in FIG. 3, the collar is arranged at or near the proximal end of the first rod part 30. The collar 35 protrudes radially outward and annularly surrounds the rest of the first rod part 30. A proximally oriented, plane and annular abutment surface 36 and a distally oriented, plane and annular abutment surface 37 are provided on the collar 35.

The shaft tube 50 has a channel 52. The cross section of the channel 52 in the shaft tube 50 and the cross section of the wire 20 are chosen such that the wire 20 is guided in the channel 52 in the shaft tube 50 with little play and in particular with little friction. The shaft tube 50 has, for example, a circular cross section and an external diameter of 2 mm or less. The wire 20 has, for example, a circular cross section and an external diameter of a few tenths of a millimeter.

The first sleeve part 60 has a substantially circular cylindrical channel in which the proximal end 56 of the shaft tube 50 is arranged and which is narrowed by a radially inwardly protruding collar 66 at the proximal end of the first sleeve part 60. The proximal end 56 of the shaft tube 50 bears on the collar 66 at a distally oriented circular surface. The collar 66 narrows the channel enclosed by the first sleeve part 60 to a cross section which approximately corresponds to or is greater than the cross section of the channel 52 in the shaft tube 50. Thus, the wire 20 can also be moved relative to the first sleeve part 60 with little friction.

The second sleeve part 70 encloses a channel 73 which extends from the distal end to the proximal end of the second sleeve part 70. The cross section of the channel 73 in the second sleeve part 70 and the cross section of the first rod part 30 are chosen such that the first rod part 30 is guided in the channel 73 in the second sleeve part 70 with little play and little friction.

The channel 73 in the second sleeve part 70 is widened at one location by a radially outwardly extending groove in which an O-ring 74 is arranged. The groove, the O-ring 74 and the outer contour of the cross section of the first rod part 30 are chosen such that the O-ring 74 bears at any given time on the outer jacket surface of the first rod part 30. The O-ring 74 can in this way suppress or at least impede crossover of a fluid from distal to proximal. Moreover, the O-ring 74 can brake a movement of the transmission device 20, 30, 40 relative to the shaft 50, 60, 70, 80. To simplify the production of the groove for the O-ring 74, the cross section of the channel 73 in the second sleeve part 70 is greater in the distal direction from the groove than in the proximal direction from the groove.

The cross section of the channel 73 in the second sleeve part 70 is widened in a step shape near the distal end of the second sleeve part 70 in order to receive the first sleeve part 60 and to positively define the position of the first sleeve part 60 relative to the second sleeve part 70. The first sleeve part 60 is fitted in the distal end of the channel 73 in the second sleeve part 70 in particular by means of a screw connection and/or in another manner involving form-fit or force-fit engagement and/or cohesive bonding.

The third sleeve part 80 has a channel 83 in which in particular the second rod part 40 is arranged. The cross section of the channel 83 in the third sleeve part 80 and the outer contour of the cross section of the second rod part 40 are chosen such that the second rod part 40 is guided with little play, and in particular with little friction, in the channel 83 in the third sleeve part 80.

The proximal end of the second sleeve part 70 and the distal end of the third sleeve part 80 are connected rigidly to each other. In the example shown, the proximal end of the second sleeve part 70 and the distal end of the third sleeve part 80 are both tubular, but with different diameters. The tubular proximal end of the second sleeve part 70 engages in the tubular distal end of the third sleeve part 80 and is joined thereto with form-fit engagement, force-fit engagement and/or cohesive bonding.

A distal step-shaped widening of the channel 83 in the third sleeve part 80 forms an annular recess 85 in the shape of a shallow groove protruding radially outward from the channel 83 in the third sleeve part 80. The collar 35 on the first rod part 30 is arranged in the recess 85. The cross section of the recess 85 and the outer contour of the collar 35 on the first rod part are chosen such that the collar 35 can be moved in the recess 85 with little friction.

The distally oriented, annular and plane region of the surface of the recess 85 forms a distally oriented abutment surface 86. Mechanical contact between the proximally oriented abutment surface 36 on the collar 35 on the first rod part 30 and the distally oriented abutment surface 86 in the recess 85 limits a movement of the transmission device 20, 30, 40 relative to the shaft 50, 60, 70, 80 in the proximal direction.

The proximally oriented, annular and plane edge face of the second sleeve part 70 forms the distal edge of the recess 85 and a proximally oriented abutment surface of the shaft 50, 60, 70, 80. Mechanical contact between the distally oriented abutment surface 37 on the collar 35 on the first rod part 30 and the proximally oriented abutment surface 78 on the shaft 50, 60, 70, 80 limits a movement of the transmission device 20, 30, 40 relative to the shaft 50, 60, 70, 80 in the distal direction.

The connector part 90 has an irrigation attachment 95 which corresponds in particular to the Luer lock system. The irrigation attachment 95 is aligned with an irrigation opening 59 in the shaft tube 50 and permits delivery of an irrigation fluid into the space between the wire 20 and the shaft tube 50 in order to clean the component.

Figure 4:
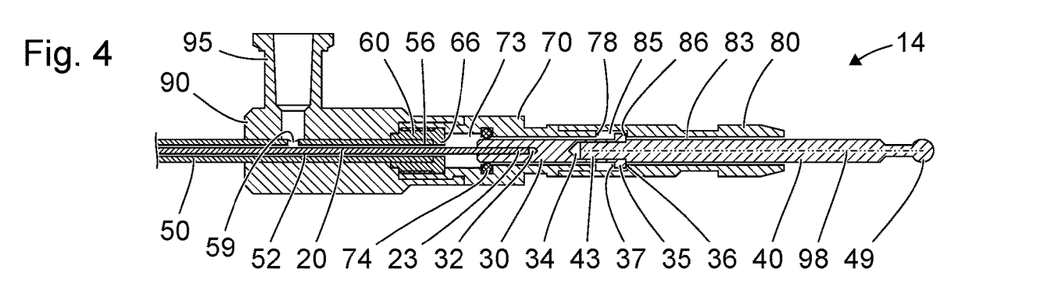
FIG. 4 is a further schematic view of a section through the proximal end of the component from FIG. 3.

FIG. 4 shows another schematic view of a section through the proximal end of the component shown in FIG. 3. The section plane of FIG. 4 corresponds to the section plane of FIG. 3.

FIG. 4 shows a situation or configuration in which the proximally oriented abutment surface 36 on the collar 35 on the transmission device 20, 30, 40 bears on the distally oriented abutment surface 86 on the shaft 50, 60, 70, 80. The position of the transmission device 20, 30, 40 relative to the shaft 50, 60, 70, 80, as shown in FIG. 4, is therefore the furthest proximal position that can be reached. When a tool (not shown in FIGS. 3 and 4) at the distal end of the component 14 has one or two movable branches or jaw parts and is provided for gripping, holding, squeezing, cutting or punching, the jaw parts of the tool bear fully on each other in the situation shown in FIG. 4 and are pressed against each other.

The component 14, in particular the position of the proximally oriented abutment surface 36 on the collar 35 on the transmission device 20, 30, 40 and of the distally oriented abutment surface 86 on the shaft 50, 60, 70, 80, and the elastic properties of the wire 20 are chosen such that, in the situation shown in FIG. 4, the wire 20 is only deformed elastically, not plastically, and the shaft tube 50 and the tool are also not destroyed or damaged by the forces that occur. This applies in particular even when the tool is blocked in the fully opened state, for example by a hard or unyielding object between the jaw parts.

Figure 5:
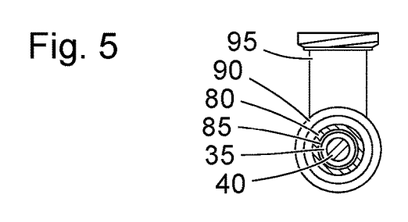
FIG. 5 is a schematic view of a further section through the proximal end of the component from FIGS. 3 and 4.

FIG. 5 shows a view of a further section through the component shown in FIGS. 3 and 4. The section plane of FIG. 5 is orthogonal to the section plane of FIGS. 3 and 4 and to the longitudinal axis and axis of symmetry of the transmission device 20, 30, 40. The section plane of FIG. 5 intersects the recess 85 and lies proximally with respect to the collar 35 on the transmission device 20, 30, 40. FIG. 5 therefore shows a situation similar to that shown in FIG. 3.

It will be seen from FIG. 5 that the collar 35 encloses the rod parts 30, 40 in a circular ring shape, and that the recess 85 likewise has a circular ring shape.

Figure 6:
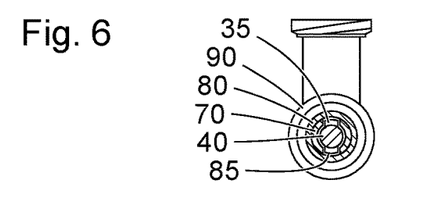
FIG. 6 is a schematic view of a section through a further component of a medical instrument.

FIG. 6 shows a schematic view of a section through a further component which, in terms of certain features, properties and functions, is similar to the component 14 shown in FIGS. 3 to 5. The section plane of FIG. 6 corresponds to the section plane of FIG. 5. The features, properties and functions that distinguish the component shown in FIG. 6 from the component shown in FIGS. 3 to 5 are in particular described below. A longitudinal section, as shown in FIGS. 3 and 4, through the component shown in FIG. 6 would not differ from the sections shown in FIGS. 3 and 4. Therefore, reference is also made below to FIGS. 3 and 4.

The component 14 shown in FIG. 6 does not have an annular recess widening the channel 30, 40 in the shaft 50, 60, 70, 80 but instead one or more niche-shaped recesses 85. In the example shown, two recesses 85 lie symmetrically opposite each other. The niche-shaped recesses 85 widen the channel 73, 83 in the shaft 50, 60, 70, 80 in which the transmission device 20, 30, 40 is arranged. In the component shown in FIG. 6, the third sleeve part 80 has in particular the same shape as in the component shown in FIGS. 3 to 5. However, the second sleeve part 70 does not have a proximal edge surface 78 with a circular ring shape but instead a stepped edge surface. The proximal edge of the second sleeve part 70 bears in particular on the distally oriented, circular-ring-shaped abutment surface 86 on the third sleeve part 80 but is interrupted by two mutually opposite slits that form the recesses 85. The distal ends of these slits form proximally oriented abutment surfaces 78 (cf. FIG. 3).

In the component shown in FIG. 6, the transmission device 20, 30, 40 does not have an annular collar, but instead two mutually opposite projections or lugs or pegs 35. The lugs 35 are arranged in the recesses 85.

In the component shown in FIG. 6, similarly to what has been described for the component shown in FIGS. 3 to 5, a mechanical contact between the lugs 35 or abutment surfaces on the lugs 35 on the transmission device 20, 30, 40 and abutment surfaces on the shaft 50, 60, 70, 80 limits a movement of the transmission device 20, 30, 40 relative to the shaft 50, 60, 70, 80 both in the proximal direction and also in the distal direction.

Figure 7:
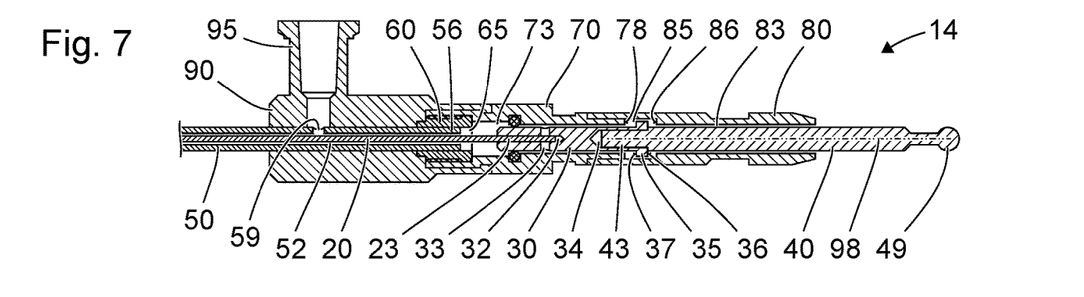
FIG. 7 is a schematic view of a section through the proximal end of a further component of a medical instrument.

FIG. 7 shows a schematic view of a section through a further component 14 which, in terms of certain features, properties and functions, is similar to the components shown in FIGS. 3 to 6. The section plane shown in FIG. 7 corresponds to the section plane of FIGS. 3 and 4. Features, properties and functions that distinguish the component 14 from the components shown in FIGS. 3 to 6 are in particular described below.

The component 14 shown in FIG. 7 can have an annular collar 35 on the transmission device 20, 30, 40 in an annular recess 85 in the shaft 50, 60, 70, 80, similarly to the component shown in FIGS. 3 to 5. Alternatively, the component 14 shown in FIG. 7 can have one or more lugs on the transmission device 20, 30, 40, said lugs being arranged in an associated recess 85 in the shaft 50, 60, 70, 80, similarly to the component shown in FIG. 6.

The component 14 shown in FIG. 7 differs from the components shown in FIGS. 3 to 6 particularly in that the first sleeve part 60 has no inwardly protruding collar at the proximal end. Rather, the channel 65 in the first sleeve part 60 is a continuous cylinder, in particular a circular cylinder. This permits a manufacture of the component 14 as shown in FIGS. 8 to 13.

Figure 8:
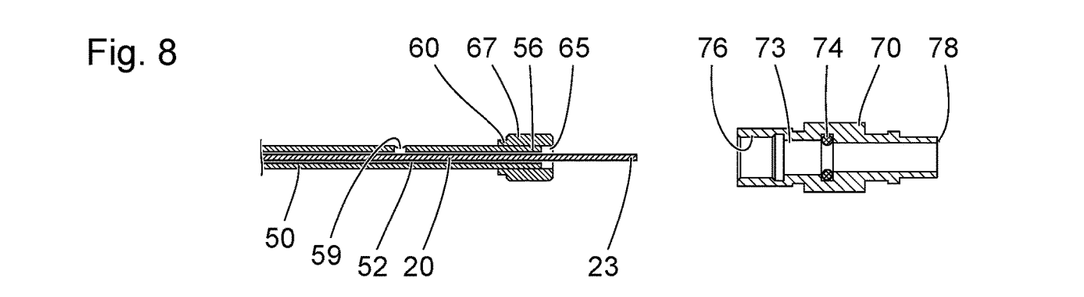
FIG. 8 is a schematic view of a section through parts of the component from FIG. 7.

FIG. 8 shows a schematic view of a section through parts of the component 14 from FIG. 7 during the manufacture thereof. The section plane of FIG. 8 corresponds to the section planes of FIGS. 3, 4 and 7.

FIG. 8 shows a situation, during the manufacture of the component, in which the wire 20 is already arranged in the channel 52 in the shaft tube 50. The proximal end 56 of the shaft tube 50 is inserted into the channel 65 in the first sleeve part 60. However, the shaft tube 50 is not yet rigidly connected to the first sleeve part 60 and instead, as is described below with reference to FIGS. 10 to 12, can be moved relative to the first sleeve part 60. The first sleeve part 60 has an outer thread 67, which is provided and designed for form-fit and force-fit engagement with a corresponding inner thread 76 at the distal end of the second sleeve part 70.

Figure 9:
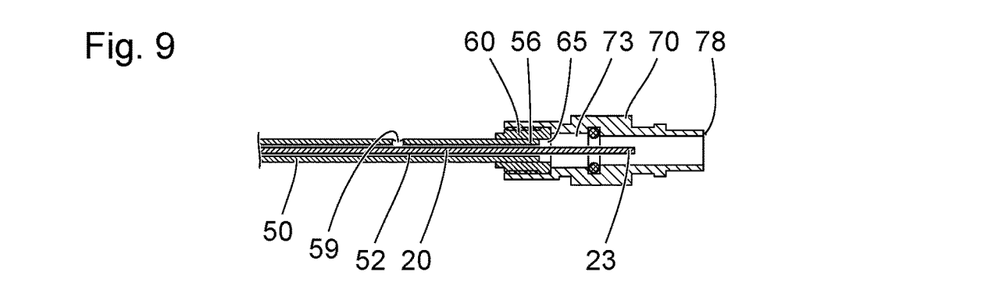
FIG. 9 is a further schematic view of a section through the parts from FIG. 8.

FIG. 9 shows a further schematic view of a section through the parts shown in FIG. 8. The section plane of FIG. 9 corresponds to the section planes of FIGS. 3, 4, 7 and 8.

In the situation shown in FIG. 9, the first sleeve part 60 is connected to the distal end of the second sleeve part 70 by a screw connection between its outer thread 67 (cf. FIG. 8) and the inner thread 76 on the second sleeve part 70. Alternatively or in addition, the first sleeve part 60 and the second sleeve part 70 can be connected to each other in another manner involving form-fit or force-fit engagement and/or cohesive bonding.

Figure 10:
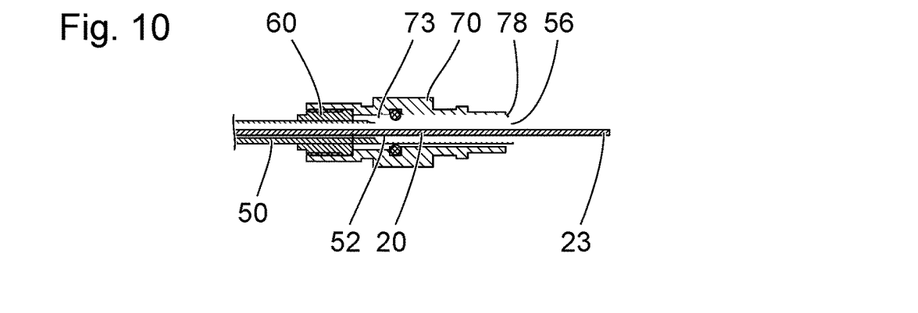
FIG. 10 is a further schematic view of a section through the parts from FIGS. 8 and 9.

FIG. 10 shows a further schematic view of a section through the parts shown in FIGS. 8 and 9. The section plane of FIG. 10 corresponds to the section planes of FIGS. 3, 4 and 7 to 9.

In the situation shown in FIG. 10, the unit composed of the first sleeve part 60 and of the second sleeve part 70 is moved in the distal direction relative to the wire 20 and the shaft tube 50, such that the proximal end 23 of the wire 20 (and optionally also the proximal end 56 of the shaft tube 50 as shown in FIG. 10) protrudes proximally from the channel 73 in the second sleeve part 70.

Figure 11:
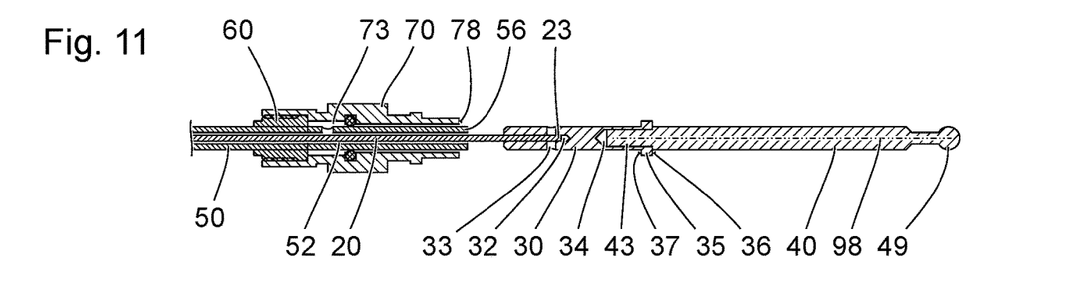
FIG. 11 is a schematic view of a section through parts of the component from FIGS. 7 to 10.

FIG. 11 shows a further schematic view of a section through parts of the component 14 shown in FIG. 7, during the manufacture of said component. The section plane of FIG. 11 corresponds to the section planes of FIGS. 3, 4 and 7 to 10.

In the situation shown in FIG. 11, the proximal end 23 of the wire 20 protruding from the second sleeve part 70 is inserted into the first longitudinal bore 32 at the distal end of the first rod part 30. In the region of the first longitudinal bore 32 in the example shown, a transverse bore 33 is provided in the first rod part 30, in order to permit or facilitate cohesive bonding of the proximal end 23 of the wire 20 to the distal end of the first rod part 30. In particular, the proximal end 23 of the wire 20 is cohesively bonded to the first rod part 30 by laser welding in the region of the transverse bore 33. Alternatively or in addition, the proximal end 23 of the wire 20 and the first rod part 30 can be connected to each other in another manner involving form-fit engagement, force-fit engagement and/or cohesive bonding.

A transverse bore 33 in the first rod part 30, as is shown in FIGS. 7 and 11, can also be provided in the components shown in FIGS. 3 to 6.

Figure 12:
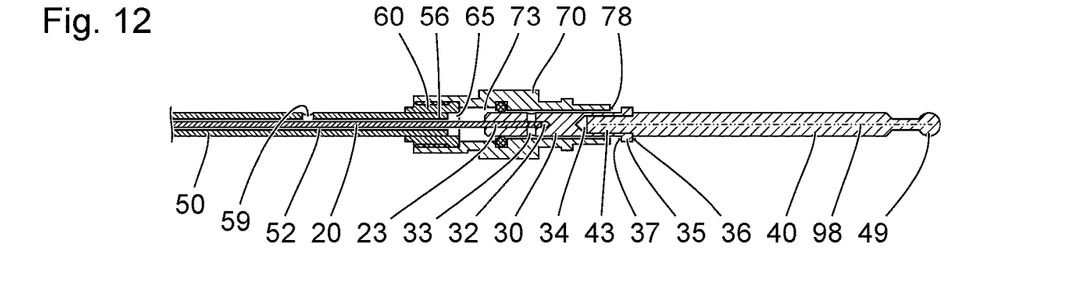
FIG. 12 is a further schematic view of a section through the parts from FIG. 11.

FIG. 12 shows a further schematic view of a section through the parts shown in FIG. 11. The section plane of FIG. 12 corresponds to the section planes of FIGS. 3, 4 and 7 to 11.

In the situation shown in FIG. 12, the unit composed of the first sleeve part 60 and of the second sleeve part 70 is moved back in the proximal direction relative to the shaft tube 50 and also relative to the transmission device 20, 30, 40. The position, shown in FIG. 12, of the unit composed of the first sleeve part 60 and of the second sleeve part 70 relative to the proximal end 56 of the shaft tube 50 corresponds to the final position, i.e. the position intended for the finished component. In this position, the proximal end 56 of the shaft tube 50 is mechanically connected rigidly to the first sleeve part 60, for example by a circumferential laser weld seam or in another manner involving form-fit engagement, force-fit engagement and/or cohesive bonding.

Figure 13:
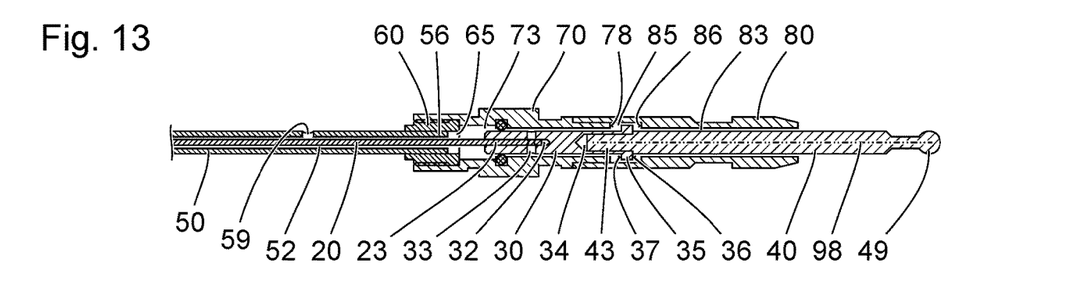
FIG. 13 is a further schematic view of a section through parts of the component from FIG. 7.

FIG. 13 shows a further schematic view of a section through parts of the component 14 shown in FIG. 7, during the manufacture of said component. The section plane of FIG. 13 corresponds to the section planes of FIGS. 3, 4 and 7 to 12.

In the situation shown in FIG. 13, the third sleeve part 80 is attached in the intended manner to the second sleeve part 70 and can be connected thereto by form-fit engagement, force-fit engagement and/or cohesive bonding. To complete the component shown in FIG. 7, all that now has to be done is to push the connector part 90 over the shaft tube 50, the first sleeve part 60 and the distal end of the second sleeve part 70 and join it thereto by form-fit engagement, force-fit engagement and/or cohesive bonding.

Figure 14:
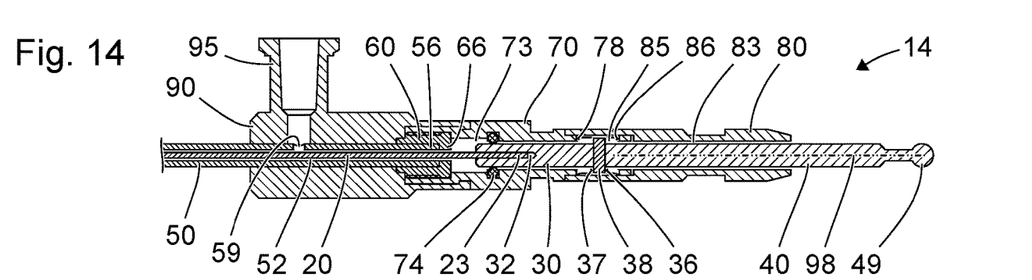
FIG. 14 is a schematic view of a section through the proximal end of a further component of a medical instrument.

FIG. 14 shows a schematic view of a section through the proximal end of a further component 14 which, in terms of certain features, properties and functions, is similar to the components shown in FIGS. 3 to 13. The section plane of FIG. 14 corresponds to the section panes of FIGS. 3, 4 and 7 to 13. Features and properties that distinguish the component 14 from the components shown in FIGS. 3 to 13 are in particular described below.

The component 14 shown in FIG. 14 differs from the components shown in FIGS. 3 to 13 in particular in that only one rod part 30 is provided, which combines the functions of both rod parts 30, 40 of the components shown in FIGS. 3 to 13. At its distal end, the rod part 30 comprises in particular a longitudinal bore 32 in which the proximal end 23 of the wire 20 is arranged and secured, and, at its proximal end, it has a coupling ball 49 for releasable mechanical coupling to a movable part 19 of the manipulation device 18 (cf. FIG. 1).

The components shown in FIGS. 3 to 13 can also each be provided with just a single rod part 30 instead of two interconnected rod parts, which single rod part 30, as in the component 14 shown in FIG. 14, itself combines all the functions of the rod parts.

The component 14 shown in FIG. 14 moreover differs from the components shown in FIGS. 3 to 13 in that neither an annular collar is provided nor one or more lugs on the rod part 30. Instead, a pin 38 is provided in a corresponding transverse bore in the rod part 30. Both ends of the pin 38 extend from the outer contour of the rod part 30 and protrude into an elongate recess 85 in the shaft 50, 60, 70, 80. Proximally oriented abutment surfaces 36 and distally oriented abutment surfaces 37 of the transmission device 20, 30, 40 are formed by corresponding parts of the surfaces of the ends of the pin 38.

The recesses 85 are formed by slits in the second sleeve part 70, which are closed off from the outside by a tubular portion of the third sleeve part 80. Edge regions of the slits forming the recesses 85 in the second sleeve part 70 form the proximally oriented abutment surface 78 and the distally oriented abutment surface 86.

Mechanical contact between the proximally oriented abutment surfaces 36 on the pin 38 and the distally oriented abutment surfaces 86 at the proximal ends of the recesses 85 limits the movement of the transmission device 20, 30, 40 relative to the shaft 50, 60, 70, 80 in the proximal direction. Mechanical contact between the distally oriented abutment surfaces 37 at the ends of the pin 38 and the proximally oriented abutment surfaces 78 at the distal ends of the recesses 85 limits the movement of the transmission device 20, 30, 40 relative to the shaft 50, 60, 70, 80 in the distal direction.

Figure 15:
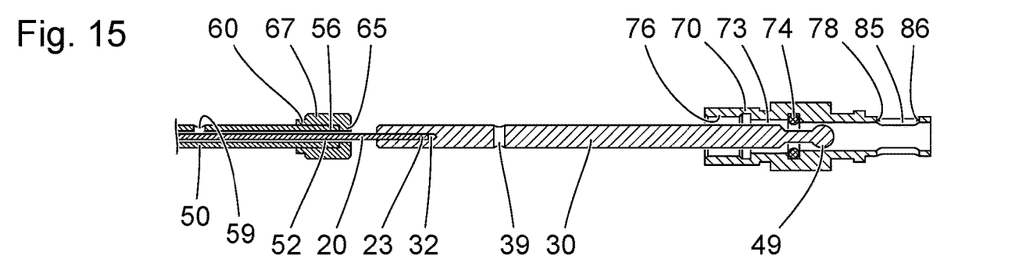
FIG. 15 is a further schematic view of a section through parts of the component from FIG. 14.

FIG. 15 shows a schematic view of a section through parts of the component shown in FIG. 14. The section plane of FIG. 15 corresponds to the section planes of FIGS. 3,4 and 7 to 14.

FIG. 15 shows a situation in which the first sleeve part 60 can already be mechanically connected rigidly to the proximal end 56 of the shaft tube 50. Moreover, the proximal end 23 of the wire 20 is already mechanically connected rigidly to the distal end of the rod part 30, namely inserted into the longitudinal bore 32 at the distal end of the rod part 30. The proximal end of the rod part 30 is already partially inserted into the channel 73 in the second sleeve part 70. Mutually opposite slits which form the recesses 85, and of which the proximal and distal ends form the distally oriented abutment surfaces 86 and the proximally oriented abutment surfaces 78, can be seen in the second sleeve part 70.

Proceeding from the situation shown in FIG. 15, the second sleeve part 70 can be moved distally relative to the other parts shown and connected to the first sleeve part 60, for example by a screw connection between an outer thread 67 on the first sleeve part 60 and an inner thread 76 on the second sleeve part 70.

Figure 16:
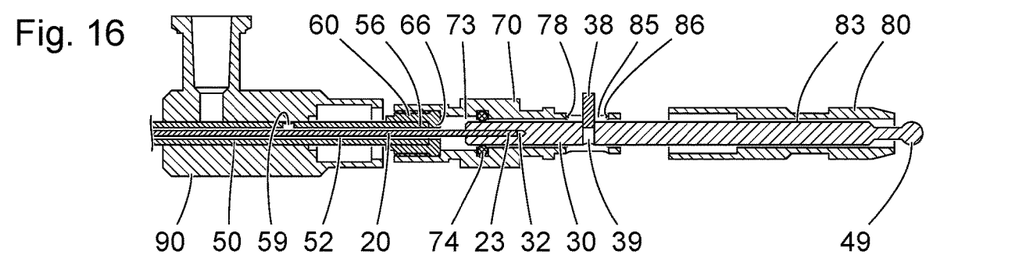
FIG. 16 is a further schematic view of a section through parts of the component from FIG. 14.

FIG. 16 shows a further schematic view of a section through parts of the component 14 shown in FIG. 14, during the manufacture of said component 14. The section plane of FIG. 16 corresponds to the section planes of FIGS. 3, 4 and 7 to 15.

The situation shown in FIG. 16 differs from the situation shown in FIG. 15 in that the first sleeve part 60 is mechanically connected rigidly and in particular permanently to the second sleeve part 70. The pin 38 is already partially inserted into a corresponding transverse bore 39 in the rod part 30 via one of the two slits on the second sleeve part 70 which form the two recesses 85. When the pin 38, relative to the rod part 30, has reached its intended position as shown in FIG. 14, the third sleeve part 80 already pushed over the proximal end of the rod part 30 in FIG. 16 can be attached to the proximal end of the second sleeve part 70 and connected mechanically rigidly and in particular permanently thereto.

Before this or thereafter, the connector part 90 can also be pushed from the distal direction over the first sleeve part 60 and the distal end of the second sleeve part 70. In the examples shown in FIGS. 3 to 16, a mechanically rigid connection between the connector part 90 and the second sleeve part 70 is in each case formed by an inwardly protruding collar at the proximal end of the connector part 90 engaging in a corresponding circumferential groove on the second sleeve part 70. Alternatively or in addition, in all of the components 14 shown in FIGS. 3 to 16, the connector part 90 can be joined to the shaft tube 50 and/or to the second sleeve part 70 by form-fit engagement, force-fit engagement and/or cohesive bonding.

Figure 17:
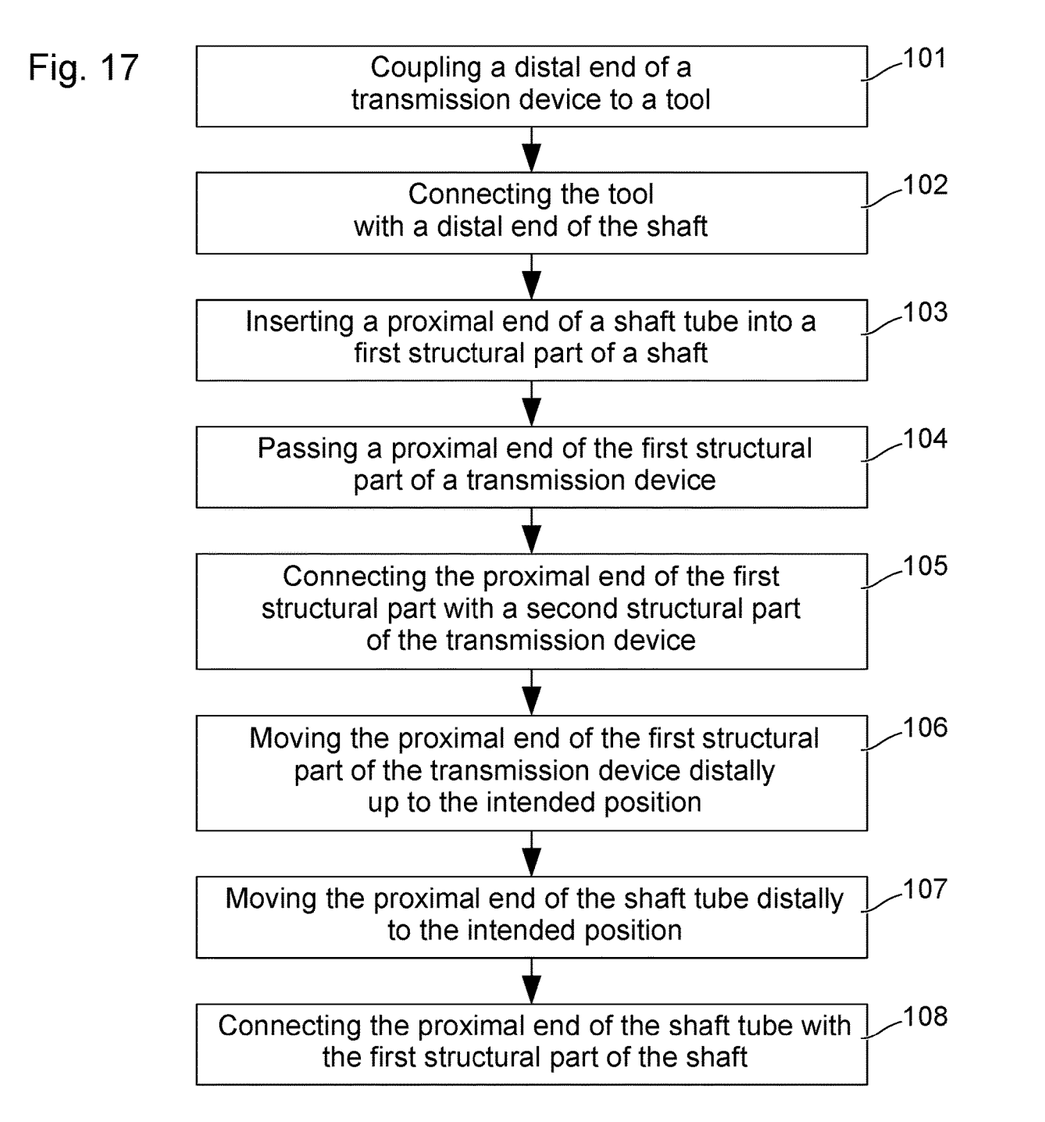
FIG. 17 is a schematic flowchart of a method for producing a component for a medical instrument.

FIG. 17 shows a schematic flowchart of a method for producing a component for a medical instrument, in particular one of the components shown in FIGS. 3 to 16. The method is also suitable for producing a component having features, properties and functions that deviate from those shown in FIGS. 1 to 16. However, in order to make matters clearer, reference signs from FIGS. 1 to 16 are used below by way of example.

In a first step 101, a distal end of a transmission device 16, 20, 30, 40 is coupled to a movable part of a tool 13. The tool 13 is provided in particular for gripping, holding, squeezing, cutting or punching and has, for example, a stationary branch or a stationary jaw part, and a branch that is pivotable relative to the stationary branch. The pivotable branch can be coupled to the distal end of the transmission device 16, 20, 30, 40 directly by a hinge or indirectly via a connecting rod. Alternatively, the pivotable branch can be coupled to the distal end of the transmission device 16, 20, 30, 40 in such a way that a translation of the transmission device 16, 20, 30, 40 brings about a pivoting movement of the pivotable branch.

In a second step 102, the tool 13 is connected to the distal end of the shaft 15, 50, 60, 70, 80. In the second step 102, the tool is connected to the distal end of the shaft 15, 50, 60, 70, 80 in particular permanently, i.e. such that it is not releasable without destruction.

In a third step 103, a proximal end 56 of a shaft tube 50 is inserted into the first structural part 60, 70 of the shaft 15, 50, 60, 70, 80 as far as an assembly position (cf. FIGS. 10 and 11) relative to a first structural part 60, 70 of a shaft 15, 50, 60, 70, 80 to be produced as part of the component to be produced. The assembly position of the proximal end 56 of the shaft tube 50 (c.f. FIGS. 10 and 11) is situated proximally with respect to the position (cf. FIG. 7), intended for the finished component, of the proximal end 56 of the shaft tube 50 relative to the first structural part 60, 70 of the shaft 15, 50, 60, 70, 80. The assembly position of the proximal end 56 of the shaft tube 50 can be situated proximally (cf. FIGS. 10 and 11) or distally from the proximal end of the first structural part 60, 70 of the shaft 15, 50, 60, 70, 80.

In a fourth step 104, a proximal end 23 of a first structural part 20 of a transmission device 16, 20, 30, 40 is guided from the distal direction as far as an assembly position (cf. FIGS. 10 and 11) through the first structural part 60, 70 of the shaft 15, 50, 60, 70, 80. The assembly position of the proximal end 23 of the first structural part 20 relative to the first structural part 60, 70 of the shaft 15, 50, 60, 70, 80 lies proximally with respect to its position (cf. FIG. 7) intended for the finished component 14. The assembly position of the proximal end 23 of the first structural part 20 of the transmission device 16, 20, 30, 40 lies in particular proximally with respect to the proximal end of the first structural part 60, 70 of the shaft 15, 50, 60, 70, 80.

The first step 101, the second step 102, the third step 103 and the fourth step 104 are in particular carried out in the stated order. Alternatively, these steps can also be carried out in another order, wherein the first step 101 and the second step 102 are in particular carried out before the third step 103 and/or before the fourth step 104. If the first step 101 and the second step 102 are carried out before the third step 103 and the fourth step 104, the third step 103 and the fourth step 104 can be carried out simultaneously. The first step 101, the second step 102 and the third step 103 are each optional and can be omitted.

In a fifth step 105, the proximal end 23 of the first structural part 20 of the transmission device 16, 20, 30, 40 is mechanically connected to a second structural part 30, 40 of the transmission device 16, 20, 30, 40. The mechanical connection produced in the fifth step 105 is in particular a permanent connection, i.e. is not releasable without destruction. The second structural part 30, 40 of the transmission device 16, 20, 30, 40 and the first structural part 50, 60, 70 of the shaft 15, 50, 60, 70, 80 are in particular designed such that a movement of the second structural part 30, 40 of the transmission device 16, 20, 30, 40 relative to the first structural part 50, 60, 70 of the shaft 15, 50, 60, 70, 80 is limited in the distal direction by mechanical contact of corresponding abutment surfaces 37, 78.

In a sixth step 106, proceeding from the assembly position of the proximal end 23 of the first structural part 20, the proximal end 23 of the first structural part 20 of the transmission device 16, 20, 30, 40 is moved distally as far as a position, intended for the finished component, relative to the first structural part 60, 70 of the shaft 15, 50, 60, 70, 80.

In a seventh step 107, the proximal end 56 of the shaft tube 50 is moved distally relative to the first structural part of the shaft 15, 50, 60, 70, 80, as far as the position intended for the use of the component 14.

The sixth step 106 and the seventh step 107 are in particular carried out simultaneously or in any desired order, but both after the fourth step 104 and the fifth step 105.

In an eighth step 108, the proximal end 56 of the shaft tube 50 is connected to the first structural part 60, 70 of the shaft 15, 50, 60, 70, 80. The eighth step 108 is in particular carried out after the seventh step 107, i.e. in the position, provided for the finished component 14, of the proximal end 56 of the shaft tube 50 relative to the first structural part 60, 70 of the shaft 15, 50, 60, 70, 80.

While specific embodiments of the invention have been shown and described in detail to illustrate the application of the principles of the invention, it will be understood that the invention may be embodied otherwise without departing from such principles.

The invention claimed is:

1. A component for a medical instrument, the component comprising:
   a shaft;
   a transmission device, which is movable in the shaft, for transmitting a force from a manipulation device coupled to the proximal end of the component to a tool at the distal end of the component;
   an abutment surface on the shaft; and
   an abutment surface on the transmission device, wherein the abutment surface of the shaft and the abutment surface of the transmission device are arranged such that a mechanical contact between the abutment surface of the transmission device and the abutment surface of the shaft limits a movement of the transmission device relative to the shaft in a proximal end direction, the transmission device having a transmission device minimum cross-sectional surface area in a portion of the transmission device lying distally with respect to the abutment surface of the transmission device, wherein all cross-sectional surface areas of the transmission device lying proximally with respect to the abutment surface of the transmission device are greater than the minimum cross-sectional surface area of the transmission device.

2. The component as claimed in claim 1, wherein:
   the abutment surface of the shaft and the abutment surface of the transmission device are arranged such that a mechanical contact between the abutment surface of the transmission device and the abutment surface of the shaft, during the intended use, limits an elastic deformation of the transmission device, caused by a force transmitted by the transmission device, to a predetermined maximum value to prevent destruction or damage of the shaft, the transmission device and a tool connected to the distal end of the shaft and coupled to the distal end of the transmission device.

3. The component as claimed in claim 2, wherein destruction or damage of the shaft, the transmission device and a tool coupled to the distal end of the shaft is prevented when the tool is blocked in a fully opened state or in a fully closed state or in any desired state.

4. The component as claimed in claim 1, wherein the abutment surface of the shaft is arranged near the proximal end of the shaft, and the abutment surface of the transmission device is arranged near the proximal end of the transmission device.

5. The component as claimed in claim 1, wherein:
the transmission device, distally with respect to the abutment surface of the transmission device, is elastically deformable up to a first maximum force,
the transmission device, proximally with respect to the abutment surface of the transmission device, is elastically deformable up to a second maximum force,
the second maximum force is greater than the first maximum force.

6. The component as claimed in claim 1, further comprising:
a further abutment surface on the shaft;
a further abutment surface on the transmission device, wherein the further abutment surface of the shaft and the further abutment surface of the transmission device are arranged such that a mechanical contact between the further abutment surface of the transmission device and the further abutment surface of the shaft limits a movement of the transmission device relative to the shaft in a direction of the distal end.

7. The component as claimed in claim 1, wherein:
the transmission device has an outwardly protruding collar,
the shaft has a groove which widens a channel in which the transmission device is arranged,
the collar of the transmission device is arranged in the groove of the shaft,
the abutment surface of the shaft is part of the inner surface of the groove, and
the abutment surface of the transmission device is part of the surface of the collar.

8. The component as claimed in claim 1, wherein:
the transmission device has a projection, a lug, a web, a peg or another convex region,
the shaft has a groove or another niche-shaped recess, which issues from a channel wherein the transmission device is arranged,
the projection or the lug or the web or the peg or the other convex region of the transmission device is arranged in the groove or the other niche-shaped recess of the shaft,
the abutment surface of the shaft is part of the inner surface of the groove or of the other niche-shaped recess of the shaft,
the abutment surface of the transmission device is part of the surface of the projection or of the lug or of the peg or of the other convex region.

9. The component as claimed in claim 1, further comprising:
a tool at the distal end of the shaft, wherein the tool has a movable structural part which is coupled to the distal end of the transmission device.

10. A medical instrument comprising:
a component; and
a manipulation device, wherein the component comprises comprising a shaft, a transmission device, which is movable in the shaft, for transmitting a force from the manipulation device coupled to the proximal end of the component to a tool at the distal end of the component, an abutment surface on the shaft and an abutment surface on the transmission device, wherein the abutment surface of the shaft and the abutment surface of the transmission device are arranged such that a mechanical contact between the abutment surface of the transmission device and the abutment surface of the shaft limits a movement of the transmission device relative to the shaft in a proximal end direction, the transmission device having a transmission device minimum cross-sectional surface area in a portion of the transmission device lying distally with respect to the abutment surface of the transmission device, wherein all cross-sectional surface areas of the transmission device lying proximally with respect to the abutment surface of the transmission device are greater than the minimum cross-sectional surface area of the transmission device; and
the manipulation device is coupled or couplable to the proximal end of the shaft.

11. A medical instrument according to claim 10, wherein:
the abutment surface of the shaft and the abutment surface of the transmission device are arranged such that a mechanical contact between the abutment surface of the transmission device and the abutment surface of the shaft, during use, limits an elastic deformation of the transmission device, caused by a force transmitted by the transmission device, to a predetermined maximum value to prevent destruction or damage of the shaft, the transmission device and a tool connected to the distal end of the shaft and coupled to the distal end of the transmission device.

12. A medical instrument according to claim 11, wherein destruction or damage of the shaft, the transmission device and a tool coupled to the distal end of the shaft is prevented when the tool is blocked in a fully opened state or in a fully closed state or in any desired state.

13. A medical instrument according to claim 11, wherein the component further comprises:
a further abutment surface on the shaft; and
a further abutment surface on the transmission device, wherein the further abutment surface of the shaft and the further abutment surface of the transmission device are arranged such that a mechanical contact between the further abutment surface of the transmission device and the further abutment surface of the shaft limits a movement of the transmission device relative to the shaft in a direction of the distal end.

14. A method for producing a component for a medical instrument, the method comprising the steps of:
guiding a proximal end of a first structural part of a transmission device through a first structural part of a shaft to an assembly position, the transmission device comprising an abutment surface, the transmission device having a transmission device minimum cross-sectional surface area in a portion of the transmission device lying distally with respect to the abutment surface of the transmission device, wherein all cross-sectional surface areas of the transmission device lying proximally with respect to the abutment surface of the transmission device are greater than the minimum cross-sectional surface area of the transmission device;

mechanically connecting the proximal end of the first structural part of the transmission device to a second structural part of the transmission device; and moving the proximal end of the first structural part of the transmission device, relative to the first structural part of the shaft.

15. The method as claimed in claim 14, further comprising the following steps:

before connecting the proximal end of the first structural part of the transmission device to the second structural part of the transmission device, moving the proximal end of the shaft tube relative to the first structural part of the shaft and mechanically connecting the proximal end of the shaft tube to the first structural part of the shaft.

16. The method as claimed in claim 15, further comprising the steps of:

coupling a distal end of the transmission device to a movable part of a tool; and mechanically connecting the tool to a distal end of the shaft.

17. The method as claimed in the claim 16, wherein at least the step of coupling the distal end of the transmission device to a movable part of the tool is carried out at least either before the step of inserting the proximal end of the shaft tube into the first structural part of the shaft or before the step of guiding the proximal end of the first structural part of the transmission device through the first structural part of the shaft.

18. The method as claimed in claim 14, further comprising the steps of:

coupling a distal end of the transmission device to a movable part of a tool; and mechanically connecting the tool to a distal end of the shaft.

19. The method as claimed in claim 18, wherein at least either the step of coupling the distal end of the transmission device to a movable part of the tool or the step of mechanically connecting the tool to the distal end of the shaft is carried out at least either before the step of inserting the proximal end of the shaft tube into the first structural part of the shaft or before the step of guiding the proximal end of the first structural part of the transmission device through the first structural part of the shaft.

* * * * *